US007091003B1

(12) United States Patent
Harris et al.

(10) Patent No.: US 7,091,003 B1
(45) Date of Patent: Aug. 15, 2006

(54) POLYPEPTIDES HAVING PHOSPHOLIPASE B ACTIVITY AND NUCLEIC ACIDS ENCODING SAME

(75) Inventors: Paul Harris, Davis, CA (US); Kimberly M. Brown, Elk Grove, CA (US)

(73) Assignee: Novozymes, Inc., Davis, CA (US)

( * ) Notice: Subject to any disclaimer, the term of this patent is extended or adjusted under 35 U.S.C. 154(b) by 0 days.

(21) Appl. No.: 09/615,571

(22) Filed: Jul. 13, 2000

Related U.S. Application Data

(62) Division of application No. 09/426,072, filed on Oct. 21, 1999, now Pat. No. 6,146,869.

(51) Int. Cl.
*C12P 21/02* (2006.01)
*C12N 1/15* (2006.01)
*C12N 1/20* (2006.01)
*C12N 15/55* (2006.01)
*C12N 15/70* (2006.01)
*C12N 15/80* (2006.01)
*C07H 21/04* (2006.01)
*C12N 9/20* (2006.01)

(52) U.S. Cl. ............. 435/69.1; 435/320.1; 435/254.11; 435/252.3; 435/471; 435/198; 536/23.1; 536/23.2; 536/23.7; 536/23.74; 536/24.1

(58) Field of Classification Search ............... 536/23.1, 536/23.2, 23.7, 23.74, 24.1, 24.3, 24.32; 435/198, 6, 69.1, 326.1, 254.11, 257.3, 471; 530/350
See application file for complete search history.

(56) References Cited

U.S. PATENT DOCUMENTS 5,965,422 A * 10/1999 Loffler et al. ................ 435/198

FOREIGN PATENT DOCUMENTS

WO WO 98/26057 6/1998

OTHER PUBLICATIONS

Agnan et al., Cloning Heterologous Gene: Problems and Approches, 1997, Fungal Genetics and Biology, vol. 21, pp. 292-301.*
Ngo et al., "Computational complexity, protein structure prediction, and the Levinthal paradox", in The Protein Folding Problem and Tertiary Structure Prediction, Merz et al. (eds.), Birkhauser Boston: Boston, MA, pp. 433 and 492-495.*

Rudinger, "Characteristics of the amino acid as componants of a peptide hormone sequence", in Peptide Hormones, Parsons (ed.), University Park Press: Baltimore, MD, pp. 1-7.*
Lee et al., "The Saccharomyces cerevisiae PLB 1 gene encodes a protein required for lysophosphplipase and phopholipase B activity," J. Biol. Chem. 269 (31): 19725-19730, Aug. 1994.*
www.chem.qmul.ac.uk/iubmb/enzyme/EC3/1/—"Enzyme Nomenclature. Recommendations EC 3.1, acting on ester bonds," Nomenclature Committee of the INternational Union of Biochemistry and Molecular Biology (NC-IUBMB).*
www.chem.qmul.ac.uk/iubmb/enzyme/EC3/1/1/— "Enzyme Nomenclature. Recommendations EC3.1.1, Carboxylic Ester Hydrolases," Nomenclature Committee of the INternational Union of Biochemistry and Molecular Biology (NC-IUBMB).*
www.chem.qmul.ac.uk/iubmb/enzyme/EC3/1/4/— "Enzyme Nomenclature. Recommendations EC 3.1.1, Phosphoric Diester Hydrolases," Nomenclature Committee of the INternational Union of Biochemistry and Molecular Biology (NC-IUBMB).*
Saito et al., 1991, Methods in Enzymology 197: 446-456.
Chen et al., Infection & Immunity 65: 405-411.
Fifis et al., 1996, Veterinary Microbiology 49: 219-233.
Kawaski, 1975, Journal of Biochemistry 77: 1233-1244.
Masuda et al., European Journal of Biochemistry 202: 783-787.
Mustranta et al., 1995, Process Biochemistry 30: 393-401.
Ichimasa et al., 1985, Agric. Biol. Chem. 49: 1083-1089.
Lee et al., 1994, Journal of Biological Chemistry 269: 19725-19730.
Kuwabara, 1998, Agric. Biol. Chem. 52: 2451-2458.
Watanabe et al., 1994, FEMS Microbiological Letters 124: 29-34.
Oishi et al., 1996, Biosci. Biotech. Biochem. 60:1087-1092.
Chakravarti et al., 1981, Archives of Biochemistry & Biophysics 206: 393-402.
Uehara et al., 1979, Agric. Biol. Chem. 43: 517-525.

* cited by examiner

*Primary Examiner*—Scott D. Priebe
(74) *Attorney, Agent, or Firm*—Robert L. Stames

(57) ABSTRACT

The present invention relates to isolated polypeptides having phospholipase B activity and isolated nucleic acid sequences encoding the polypeptides. The invention also relates to nucleic acid constructs, vectors, and host cells comprising the nucleic acid sequences as well as methods for producing and using the polypeptides.

15 Claims, 2 Drawing Sheets

```
AATTCCTGGACAACAATCCCTTTGAGAGTGATAGTAAGGGGATGAACTGAGATGCTAAGCTCACGTTCTTC    72
GCCTTGGCGTAGGCTGCCCCATGTCTTGTGTTTAGTGCTTCTCTCCACCGTTAGCTTAGCCATTGCTTGTC   144
CAATCCCACTTCCCATCTCGCATCACGCTCTATTTATGACCAAGGCTGTCAAATGAGAGCCCACTCATGTGG  216
CCTCCACTTCATATTGTTTCTTTGTCGATAAGACTGTCATCCCGGTGCTCCCGTTGCTTCCACGAAGAACGAT 288
TTGTAAAGATGGATAGCGATAGGCGACACAGTCGGTATCCGAATGGGACAGCATTGTTCAAGCTCTCGATATA 360
GCGCTTCAACCCGACGCACAGCGCTCAGACTCCTCTACTGCTCTCTTTGGCCTTCTCGGCTCTTGTGCTTGCT 432
TAAGCCTTTCCTGCCGGCGCCCGGGCTACAGCCCGCCTCTCTACTGGTCTCGGCCTCTTGCCTTCTTCCGCGA 504
GTAAACATGAAGTCCACGCTCCTGCTCTGTCTTGGTCTGGGCTTGGCCTCTGCATCGGTCTTGCTAGCCCTGTC 576
                M  K  S  T  A  L  L  T  G  L  G  L  L  A  S  L  G  L  L  A  S  P  V
ACGTCCGAGTATACGAGCGTGCGAGAAGCCTGCGGATACAAGCCTGGCTCCAAGGAGTCCATTGAGAAC       648
 T  S  E  Y  T  S  V  R  E  A  P  F  G  Y  K  P  G  S  K  E  S  I  E  N
TTGAAGGACAAGGTCGAGAACATTGTCTGGCTTATTCTCGAGAACAGGTTTGTGTGCCCTTACGATATTCAT   720
 L  K  D  K  V  E  N  I  V  W  L  I  L  E  N  R
ATGGTGAATAATAAATTCCTCAATTCAGCTTGTGGTATGTGAAGACGAGCACTAACATATGGTCCAGATCCT   792
                                                                 S
TCGATAACATTCTGGGAGGCGTGCGCCGCCAAGGACTGGACAACCCGATCAACAACGGCCCGTTCTGCAACT   864
 F  D  N  I  L  G  G  V  R  R  Q  G  L  D  N  P  I  N  N  G  P  F  C  N
ACAAGAATGCGAGCGACCCATCCTCCGGGCAAGTACTGCAAGGACTATGATTCCGTGTTCAACG           936
 Y  K  N  A  S  D  P  S  S  G  K  Y  C  T  Q  A  K  D  Y  D  S  V  F  N
ATCCAGACCACTCCGTGACTGGTAATAACTTGGAGTTCTACGGAACTTACACCCCAAACAATGGTGCGATTG   1008
 I  Q  D  H  S  V  T  G  N  N  L  E  F  Y  G  T  Y  T  P  N  N  G  A  I
CCAGTGGCAAGGTCGTCGCCGACCAGTCTGGCTTCCTCAACGCACAGCTTAACGACTACCCCAAACTGGCCC   1080
 A  S  G  K  V  V  A  D  Q  S  G  F  L  N  A  Q  L  N  D  Y  P  K  L  A
CAGAAGAGGCGACAAGGCAAGTGATGGGATACTATACGGAGGAGGAGGTTCCTACGCTCGTGGACCTTGTGG   1152
 P  E  E  A  T  R  Q  V  M  G  Y  Y  T  E  E  E  V  P  T  L  V  D  L  V
ATGAGTTCACTACTTTCAACAGCTGGTTCTGTGTTCCTGGCGTAAGTGCGATAAATCTGTATATTTTA      1224
 D  E  F  T  T  F  N  S  W  F  C  V  P  G
ATTTTGACTAACGCGTTCAAAAGCCTACAACCCCAACCCGCTTGTGCCTCTGGCAGGAACCGCTGCTGGGC   1296
              P  T  N  P  N  R  L  C  A  L  A  G  T  A  A  G
ATGGCAAGAATGACGATGACTTCCTGAACTATGGTATCTCTAAGTCCATCTTCGAGGCCGCCAACGAGA     1368
 H  G  K  N  D  D  D  F  L  N  Y  G  I  S  K  S  I  F  E  A  A  N  E
```

Fig. 1A

```
AGGGGGTGTCCTGGCTCAACTACGATGGCACCAACGGAGAATTCTTCTTCACCTACG  1440
 K  G  V  S  W  L  N  Y  D  G  T  N  G  E  F  F  T  Y
TCAACCAGACCTCCCGGTCCAACGTGGTGCCCGTTGAAAACTTCTTCCAAGACGCCTACCTCGGTGTCCTCC  1512
 V  N  Q  T  S  R  S  N  V  P  V  E  N  F  F  Q  D  A  Y  L  G  V  L
CTAAATTCTCTTACATTAACCCCTCCTGCGGCAACAACTCCATGCACCCCACCGGTAACGTCT  1584
 P  K  F  S  Y  I  N  P  S  C  G  T  N  S  M  H  P  T  G  N  V
CCTACGGTGAGGTCTTCGTCAAGCAGATCTATGATGCCCAGGCCCTCAGTGGGACAAGACCCTGC  1656
 S  Y  G  E  V  F  V  K  Q  I  Y  D  A  I  R  Q  G  P  Q  W  D  K  T  L
TCTTCATTACCTACGACGAGACTGGCTTCTACGACCATGTCCCCCCGCCCCTCGCCGTCCGCCCGGACA  1728
 L  F  I  T  Y  D  E  T  G  F  Y  D  H  V  P  P  P  L  A  V  R  P  D
ACCTGAGACTACACTGCGAAGAACGGTTCAGAAATACACTCTTTCACTTCGACCGTCTGGGCGGCA  1800
 N  L  T  Y  T  E  T  A  K  N  G  Q  K  Y  T  L  H  F  D  R  L  G  G  R
TGCCGACCTGGGTTATCTCCCCTTACAGTAAGAAGGGATACATCGAGCAGTACATGGAACGGATCCCGTCACGG  1872
 M  P  T  W  V  I  S  P  Y  S  K  K  G  Y  I  E  Q  Y  G  T  D  P  V  T
GCAAGCCCGCTACAGTGCTACCCTCCGTTCCGTCAAGACTCTCTGGGACACATCGAGGACTTCA  1944
 G  K  P  A  P  Y  S  A  T  S  V  L  K  T  L  G  D  I  E  D  F
CCCCTCGTGTCGCCCACTCTTTCGATCACCTTGGCGTGAGGATGCTCCTATTG  2016
 T  P  R  V  A  H  S  P  S  F  D  H  L  I  G  T  L  R  E  D  A  P  I
CTCTCAAGACTCCCATACCTTTCGGTATAAGTCTCAGTCCGTGAGACAGGATTAAAAGTGATGAT  2088
 A  L  K  T  P  H  T  F  S  V  .
GAACGTTCTGACTTCAGTGAACGATTACATGTTTATAGAGCATTGTTTTGCTTATAGCGCCTAGAGCGAG  2160
CGCGATGATGATAAGATAAAGCTGGGTTATTTCTTATTGTATATTCATTAATGAAAGACTTTGATAACATG  2232
GGATTAAAAGGAAATGTTTTCTTGCACAATCAACTCACGGAACAGGCGTAACTTTACGATGACTGCACCC  2304
CGGATACATTAATT 2318
```

Fig. 1B

POLYPEPTIDES HAVING PHOSPHOLIPASE B ACTIVITY AND NUCLEIC ACIDS ENCODING SAME

CROSS-REFERENCE TO RELATED APPLICATION

This application is a divisional of U.S. application Ser. No. 09/426,072 filed Oct. 21, 1999, now U.S. Pat. No. 6,146,869, which application is fully incorporated herein by reference.

BACKGROUND OF THE INVENTION

1. Field of the Invention

The present invention relates to isolated polypeptides having phospholipase B activity and isolated nucleic acid sequences encoding the polypeptides. The invention also relates to nucleic acid constructs, vectors, and host cells comprising the nucleic acid sequences as well as methods for producing and using the polypeptides.

2. Description of the Related Art

Phospholipases are enzymes that participate in the hydrolysis of phospholipids which consist of a glycerol backbone with two fatty acids in an outer (sn-1) and the middle (sn-2) positions and esterified with phosphoric acid in the third position. The phosphoric acid may, in turn, be esterified to an amino alcohol.

Several types of phospholipase activity can be distinguished which hydrolyze the fatty acyl moieties. Phospholipase A1 and A2 catalyze the deacylation of one fatty acyl group in the sn-1 and sn-2 positions, respectively, from a diacylglycerophospholipid to produce lysophospholipid. Lysophospholipase (also called phospholipase B by the Nomenclature Committee of the International Union of Biochemistry on the Nomenclature and Classification of Enzymes {Enzyme Nomenclature, Academic Press, New York, 1992}) catalyzes the hydrolysis of the remaining fatty acyl group in a lysophospholipid. A phospholipase B has been reported from *Penicillium notatum* (Saito et al., 1991, *Methods in Enzymology* 197:446–456) which catalyzes the deacylation of both fatty acids from a diacylglycerophospholipid and intrinsically possesses lysophospholipase activity.

Fungal enzymes with phospholipase activity have been reported from various sources, including *Cryptococcus neoformans* (Chen et al., *Infection and Immunity* 65: 405–411), *Fusobacterium necrophorum* (Fifis et al., 1996, *Veterinary Microbiology* 49: 219–233), *Penicillium notatum* (also known as *Penicillium chrysogenum*; Kawasaki, 1975, *Journal of Biochemistry* 77: 1233–1244; Masuda et al., 1991, *European Journal of Biochemistry* 202: 783–787), *Penicillium cyclopium* (Mustranta et al., 1995, *Process Biochemistry* 30: 393–401), *Saccharomyces cerevisia* (Ichimasa et al, 1985, *Agric. Biol. Chem.* 49: 1083–1089; Paultauf et al, 1994, *Journal of Biological Chemistry* 269: 19725–19730), *Torulaspora delbrueckii* (old name *Saccharomyces rosei*, Kuwabara, 1988, *Agric. Biol. Chem.* 52: 2451–2458; Watanabe et al, 1994, FEMS *Microbiological Letters* 124: 29–34), *Schizosaccharomyces pombe* (Oishi et al., 1996, *Biosci. Biotech. Biochem.* 60: 1087–1092), *Neurospora crassa* (Chakravarti et al, 1981, *Archives of Biochemistry and Biophysics* 206: 393–402), *Aspergillus niger* (Technical Bulletin, G-zyme™ G6999, Enzyme Bio-Systems Ltd.; Mustranta et at, 1995, supra), *Corticium centrifugum* (Uehara et al, 1979, *Agric. Biol. Chem.* 43: 517–525), *Fusarium oxysporum* (WO 98/26057), and *Fusarium solani* (Tsung-Che et al, 1968, *Phytopathological Notes* 58:1437–38).

Fungal phospholipase genes have been cloned from several sources including *Penicillum notatum* (Masuda et al., 1991, supra), *Torulaspora delbrueckii* (Watanabe et al., 1994, FEMS *Microbiology Letters* 124: 29–34), *Saccharomyces cerevisiae* (Lee at al, 1994, *Journal of Biological Chemistry* 269: 19725–19730), *Aspergillus* (JP 10155493), *Neurospora crassa* (EMBL 042791), and *Schizosaccharomyces pombe* (EMBL 013857).

It is an object of the present invention to provide improved polypeptides having phospholipase B activity and nucleic acid encoding the polypeptides.

SUMMARY OF THE INVENTION

The present invention relates to isolated polypeptides having phospholipase B activity selected from the group consisting of:

(a) a polypeptide having an amino acid sequence which has at least 65% identity with amino acids 20 to 464 of SEQ ID NO. 2;

(b) a polypeptide encoded by a nucleic acid sequence which hybridizes under low stringency conditions with (i) nucleotides 568 to 2045 of SEQ ID NO. 1, (ii) the cDNA sequence contained in nucleotides 568 to 2045 of SEQ ID NO. 1, (iii) a subsequence of (i) or (ii) of at least 100 nucleotides, or (iv) a complementary strand of (i), (ii), or (iii);

(c) a variant of the polypeptide having an amino acid sequence of SEQ ID NO. 2 comprising a substitution, deletion, and/or insertion of one or more amino acids;

(d) an allelic variant of (a) or (b); and (e) a fragment of (a), (b), or (d) that has phospholipase B activity.

The present invention also relates to isolated nucleic acid sequences encoding the polypeptides and to nucleic acid constructs, vectors, and host cells comprising the nucleic acid sequences as well as methods for producing and using the polypeptides.

DESCRIPTION OF THE FIGURES

FIGS. 1A and 1B show the genomic DNA sequence and the deduced amino acid sequence of an *Aspergillus oryzae* phospholipase B (SEQ ID NOS. 1 and 2, respectively).

DETAILED DESCRIPTION OF THE INVENTION

Polypeptides Having Phospholipase B Activity

The term "phospholipase B activity" is defined herein as a carboxylic ester hydrolysis activity which catalyzes the deacylation of one or both of the fatty acyl groups in the sn-1 and sn-2 positions of a diacylglycerophospholipid. For purposes of the present invention, phospholipase B activity is determined by incubating the phospholipase with lysolecithin (or L-α-lysophosphatidylcholine) in the presence of calcium chloride at 37° C., pH 7 for 10 minutes and measuring the release of fatty acid using any method known in the art such as the NEFA C assay kit (Wako Chemicals, Richmond, Va.) according to the manufacturer's instructions. One unit of phospholipase B activity is defined as 1.0 μmole of free fatty acid produced per minute at 37° C., pH 7.0.

In a first embodiment, the present invention relates to isolated polypeptides having an amino acid sequence which has a degree of identity to amino acids 20 to 464 of SEQ ID NO. 2 (i.e., the mature polypeptide) of at least about 65%, preferably at least about 70%, more preferably at least about 80%, even more preferably at least about 90%, most preferably at least about 95%, and even most preferably at least about 97%, which have phospholipase B activity (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from amino acids 20 to 464 of SEQ ID NO. 2. For purposes of the present invention, the degree of identity between two amino acid sequences is determined by the ClustalW method using the ClustalX software (Thompson et al., 1994, *Nucleic Acids Research* 22: 4673–4680; Thompson et al., 1997, *Nucleic Acids Research* 25: 4876–4882) with a blosum weight matrix, gap opening penalty of 10, and gap extension penalty of 0.03 to 0.05.

Preferably, the polypeptides of the present invention comprise the amino acid sequence of SEQ ID NO. 2 or an allelic variant thereof; or a fragment thereof that has phospholipase B activity. In a more preferred embodiment, the polypeptide of the present invention comprises the amino acid sequence of SEQ ID NO. 2. In another preferred embodiment, the polypeptide of the present invention comprises amino acids 20 to 464 of SEQ ID NO. 2, or an allelic variant thereof; or a fragment thereof that has phospholipase B activity. In another preferred embodiment, the polypeptide of the present invention comprises amino acids 20 to 464 of SEQ ID NO. 2. In another preferred embodiment, the polypeptide of the present invention consists of the amino acid sequence of SEQ ID NO. 2 or an allelic variant thereof; or a fragment thereof that has phospholipase B activity. In another preferred embodiment, the polypeptide of the present invention consists of the amino acid sequence of SEQ ID NO. 2. In another preferred embodiment, the polypeptide consists of amino acids 20 to 464 of SEQ ID NO. 2 or an allelic variant thereof; or a fragment thereof that has phospholipase B activity. In another preferred embodiment, the polypeptide consists of amino acids 20 to 464 of SEQ ID NO. 2.

A fragment of SEQ ID NO. 2 is a polypeptide having one or more amino acids deleted from the amino and/or carboxyl terminus of this amino acid sequence. Preferably, a fragment contains at least 375 amino acid residues, more preferably at least 400 amino acid residues, and most preferably at least 425 amino acid residues.

An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

In a second embodiment, the present invention relates to isolated polypeptides having phospholipase B activity which are encoded by nucleic acid sequences which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with (i) nucleotides 568 to 2045 of SEQ ID NO. 1, (ii) the cDNA sequence contained in nucleotides 568 to 2045 of SEQ ID NO. 1, (iii) a subsequence of (i) or (ii), or (iv) a complementary strand of (i), (ii), or (iii) (J. Sambrook, E. F. Fritsch, and T. Maniatus, 1989, *Molecular Cloning, A Laboratory Manual*, 2d edition, Cold Spring Harbor, N.Y.). The subsequence of SEQ ID NO. 1 may be at least 100 nucleotides or preferably at least 200 nucleotides. Moreover, the subsequence may encode a polypeptide fragment which has phospholipase B activity. The polypeptides may also be allelic variants or fragments of the polypeptides that have phospholipase B activity.

The nucleic acid sequence of SEQ ID NO. 1 or a subsequence thereof, as well as the amino acid sequence of SEQ ID NO. 2 or a fragment thereof, may be used to design a nucleic acid probe to identify and clone DNA encoding polypeptides having phospholipase B activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

Thus, a genomic DNA or cDNA library prepared from such other organisms may be screened for DNA which hybridizes with the probes described above and which encodes a polypeptide having phospholipase B activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO. 1 or a subsequence thereof, the carrier material is used in a Southern blot. For purposes of the present invention, hybridization indicates that the nucleic acid sequence hybridizes to a labeled nucleic acid probe corresponding to the nucleic acid sequence shown in SEQ ID NO. 1, its complementary strand, or a subsequence thereof, under very low to very high stringency conditions. Molecules to which the nucleic acid probe hybridizes under these conditions are detected using X-ray film.

In a preferred embodiment, the nucleic acid probe is a nucleic acid sequence which encodes the polypeptide of SEQ ID NO. 2, or a subsequence thereof. In another preferred embodiment, the nucleic acid probe is SEQ ID NO. 1. In another preferred embodiment, the nucleic acid probe is the mature polypeptide coding region of SEQ ID NO. 1. In another preferred embodiment, the nucleic acid probe is the nucleic acid sequence contained in plasmid pPH6 which is contained in *Escherichia coli* NRRL B-30142, wherein the nucleic acid sequence encodes a polypeptide having acid phosphatase activity. In another preferred embodiment, the nucleic acid probe is the mature polypeptide coding region contained in plasmid pPH6 which is contained in *Escherichia coli* NRRL B-30142.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP40, 1× Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third embodiment, the present invention relates to variants of the polypeptide having an amino acid sequence of SEQ ID NO. 2 comprising a substitution, deletion, and/or insertion of one or more amino acids.

The amino acid sequences of the variant polypeptides may differ from the amino acid sequence of SEQ ID NO. 2 or the mature polypeptide thereof by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In a fourth embodiment, the present invention relates to isolated polypeptides having immunochemical identity or partial immunochemical identity to the polypeptide having the amino acid sequence of SEQ ID NO. 2 or the mature polypeptide thereof. The immunochemical properties are determined by immunological cross-reaction identity tests by the well-known Ouchterlony double immunodiffusion procedure. Specifically, an antiserum containing polyclonal antibodies which are immunoreactive or bind to epitopes of the polypeptide having the amino acid sequence of SEQ ID NO. 2 or the mature polypeptide thereof are prepared by immunizing rabbits (or other rodents) according to the procedure described by Harboe and Ingild, In N. H. Axelsen, J. Krøll, and B. Weeks, editors, *A Manual of Quantitative Immunoelectrophoresis*, Blackwell Scientific Publications, 1973, Chapter 23, or Johnstone and Thorpe, *Immunochemistry in Practice*, Blackwell Scientific Publications, 1982 (more specifically pages 27–31). A polypeptide having immunochemical identity is a polypeptide which reacts with the antiserum in an identical fashion such as total fusion of precipitates, identical precipitate morphology, and/or identical electrophoretic mobility using a specific immunochemical technique. A further explanation of immunochemical identity is described by Axelsen, Bock, and Krøll, In N. H. Axelsen, J. Krøll, and B. Weeks, editors, *A Manual of Quantitative Immunoelectrophoresis*, Blackwell Scientific Publications, 1973, Chapter 10. A polypeptide having partial immunochemical identity is a polypeptide which reacts with the antiserum in a partially identical fashion such as partial fusion of precipitates, partially identical precipitate morphology, and/or partially identical electrophoretic mobility using a specific immunochemical technique. A further explanation of partial immunochemical identity is described by Bock and Axelsen, In N. H. Axelsen, J. Krøll, and B. Weeks, editors, *A Manual of Quantitative Immunoelectrophoresis*, Blackwell Scientific Publications, 1973, Chapter 11.

The antibody may also be a monoclonal antibody. Monoclonal antibodies may be prepared and used, e.g., according to the methods of E. Harlow and D. Lane, editors, 1988, *Antibodies, A Laboratory Manual*, Cold Spring Harbor Press, Cold Spring Harbor, N.Y.

The polypeptides of the present invention have at least 20%, preferably at least 40%, more preferably at least 60%, even more preferably at least 80%, even more preferably at least 90%, and most preferably at least 100% of the phospholipase B activity of the mature polypeptide of SEQ ID NO. 2.

A polypeptide of the present invention may be obtained from microorganisms of any genus. For purposes of the present invention, the term "obtained from" as used herein in connection with a given source shall mean that the polypeptide encoded by the nucleic acid sequence is produced by the source or by a cell in which the nucleic acid sequence from the source has been inserted. In a preferred embodiment, the polypeptide is secreted extracellularly.

A polypeptide of the present invention may be a bacterial polypeptide. For example, the polypeptide may be a gram positive bacterial polypeptide such as a *Bacillus* polypeptide, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis,* or *Bacillus thuringiensis* polypeptide; or a *Streptomyces* polypeptide, e.g., a *Streptomyces lividans* or *Streptomyces murinus* polypeptide; or a gram negative bacterial polypeptide, e.g., an *E. coli* or a *Pseudomonas* sp. polypeptide.

A polypeptide of the present invention may be a fungal polypeptide, and more preferably a yeast polypeptide such as a *Candida, Kluyveromyces, Pichia, Saccharomyces, Schizosaccharomyces,* or *Yarrowia* polypeptide; or more preferably a filamentous fungal polypeptide such as an *Acremonium*, *Aspergillus*, *Aureobasidium*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Piromyces*, *Schizophyllum*, *Talaromyces*, *Thermoascus*, *Thielavia*, *Tolypocladium*, or *Trichoderma* polypeptide.

In a preferred embodiment, the polypeptide is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis* or *Saccharomyces oviformis* polypeptide.

In another preferred embodiment, the polypeptide is a *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola insolens*, *Humicola lanuginosa*, *Mucor miehei*, *Myceliophthora thermophila*, *Neurospora crassa*, *Penicillium purpurogenum*, *Trichoderma harzianum*, *Trichoderma koningii*, *Trichoderma longibrachiatum*, *Trichoderma reesei*, or *Trichoderma viride* polypeptide.

In another preferred embodiment, the polypeptide is an *Aspergillus aculeatus*, *Aspergillus awamori*, *Aspergillus foetidus*, *Aspergillus japonicus*, *Aspergillus nidulans*, *Aspergillus niger*, or *Aspergillus oryzae* polypeptide.

In a more preferred embodiment, the polypeptide is an *Aspergillus oryzae* polypeptide, e.g., the polypeptide with the amino acid sequence of SEQ ID NO. 2.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents. For example, taxonomic equivalents of *Aspergillus* are defined by Raper, K. D. and Fennel, D. I., 1965, *The Genus Aspergillus*, The Wilkins Company, Baltimore. *Aspergilli* are mitosporic fungi characterized by an aspergillum comprised of a conidiospore stipe with no known teleomorphic states terminating in a vesicle, which in turn bears one or two layers of synchronously formed specialized cells, variously referred to as sterigmata or phialides, and asexually formed spores referred to as conidia. Known teleomorphs of *Aspergillus* include *Eurotium*, *Neosartorya*, and *Emericella*.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

As defined herein, an "isolated" polypeptide is a polypeptide which is essentially free of other non-phospholipase B polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

Polypeptides encoded by nucleic acid sequences of the present invention also include fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Nucleic Acid Sequences

The present invention also relates to isolated nucleic acid sequences which encode a polypeptide of the present invention. In a preferred embodiment, the nucleic acid sequence is set forth in SEQ ID NO. 1. In another more preferred embodiment, the nucleic acid sequence is the sequence contained in plasmid pPH6 that is contained in *Escherichia coli* NRRL B-30142. In another preferred embodiment, the nucleic acid sequence is the mature polypeptide coding region of SEQ ID NO. 1. In another more preferred embodiment, the nucleic acid sequence is the mature polypeptide coding region contained in plasmid pPH6 that is contained in *Escherichia coli* NRRL B-30142. The present invention also encompasses nucleic acid sequences which encode a polypeptide having the amino acid sequence of SEQ ID NO. 2 or the mature polypeptide thereof, which differ from SEQ ID NO. 1 by virtue of the degeneracy of the genetic code. The present invention also relates to subsequences of SEQ ID NO. 1 which encode fragments of SEQ ID NO. 2 that have phospholipase B activity.

A subsequence of SEQ ID NO. 1 is a nucleic acid sequence encompassed by SEQ ID NO. 1 except that one or more nucleotides from the 5' and/or 3' end have been deleted. Preferably, a subsequence contains at least 1125 nucleotides, more preferably at least 1200 nucleotides, and most preferably at least 1275 nucleotides.

The present invention also relates to mutant nucleic acid sequences comprising at least one mutation in the mature polypeptide coding sequence of SEQ ID NO. 1, in which the mutant nucleic acid sequence encodes a polypeptide which consists of amino acids 20 to 464 of SEQ ID NO. 2.

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, PCR: *A Guide to Methods and Application*, Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of *Aspergillus*, or another or related organism and thus, for example, may be an allelic or species variant of the polypeptide encoding region of the nucleic acid sequence.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The present invention also relates to nucleic acid sequences which have a degree of homology to the mature polypeptide coding sequence of SEQ ID NO. 1 (i.e., nucleotides 568 to 2045) of at least about 65%, preferably about 70%, preferably about 80%, more preferably about 90%, even more preferably about 95%, and most preferably about 97% homology, which encode an active polypeptide. For purposes of the present invention, the degree of homology between two nucleic acid sequences is determined by the Wilbur-Lipman method (Wilbur and Lipman, 1983, *Proceedings of the National Academy of Science USA* 80: 726–730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=3, gap penalty=3, and windows=20.

Modification of a nucleic acid sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variant sequence may be constructed on the basis of the nucleic acid sequence presented as the polypeptide encoding part of SEQ ID NO. 1, e.g., a subsequence thereof, and/or by introduction of nucleotide substitutions which do not give rise to another amino acid sequence of the polypeptide encoded by the nucleic acid sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95–107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081–1085). In the latter technique, mutations are introduced at every positively charged residue in the molecule, and the resultant mutant molecules are tested for phospholipase B activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306–312; Smith et al., 1992, *Journal of Molecular Biology* 224: 899–904; Wlodaver et al, 1992, *FEBS Letters* 309: 59–64).

The present invention also relates to isolated nucleic acid sequences encoding a polypeptide of the present invention, which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with the nucleic acid sequence of SEQ ID NO. 1 or its complementary strand; or allelic variants and subsequences thereof (Sambrook et al., 1989, supra), as defined herein.

The present invention also relates to isolated nucleic acid sequences produced by (a) hybridizing a DNA under very low, low, medium, medium-high, high, or very high stringency conditions with (i) nucleotides 568 to 2045 of SEQ ID NO. 1, (ii) the cDNA sequence contained in nucleotides 568 to 2045 of SEQ ID NO. 1, (iii) a subsequence of (i) or (ii), or (iv) a complementary strand of (i), (ii), or (iii); and (b) isolating the nucleic acid sequence. The subsequence is preferably a sequence of at least 100 nucleotides such as a sequence which encodes a polypeptide fragment which has phospholipase B activity.

Methods for Producing Mutant Nucleic Acid Sequences

The present invention further relates to methods for producing a mutant nucleic acid sequence, comprising introducing at least one mutation into the mature polypeptide coding sequence of SEQ ID NO. 1 or a subsequence thereof, wherein the mutant nucleic acid sequence encodes a polypeptide which consists of amino acids 20 to 464 of SEQ ID NO. 2 or a fragment thereof which has phospholipase B activity.

The introduction of a mutation into the nucleic acid sequence to exchange one nucleotide for another nucleotide may be accomplished by site-directed mutagenesis using any of the methods known in the art. Particularly useful is the procedure which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used.

Nucleic Acid Constructs

The present invention also relates to nucleic acid constructs comprising a nucleic acid sequence of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid combined and juxtaposed in a manner that would not otherwise exist in nature. The term nucleic acid construct is synonymous with the term expression cassette when the nucleic acid construct contains all the control sequences required for expression of a coding sequence of the present invention. The term "coding sequence" is defined herein as a nucleic acid sequence which directly specifies the amino acid sequence of its protein product. The boundaries of a genomic coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The term "control sequences" is defined herein to include all components which are necessary or advantageous for the expression of a polypeptide of the present invention. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the DNA sequence such that the control sequence directs the expression of a polypeptide.

The control sequence may be an appropriate promoter sequence, a nucleic acid sequence which is recognized by a host cell for expression of the nucleic acid sequence. The promoter sequence contains transcriptional control sequences which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727–3731), as well as the tac promoter (DeBoer et al., 1983, *Proceedings of the National Academy of Sciences USA* 80: 21–25). Further promoters are described in "Useful proteins from recombinant bacteria" in *Scientific American*, 1980, 242: 74–94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, Yeast 8: 423–488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983–5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109–137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

In a preferred embodiment, the signal peptide coding region is nucleotides 510 to 567 of SEQ ID NO. 1 which encode amino acids 1 to 19 of SEQ ID NO. 2.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

The present invention also relates to nucleic acid constructs for altering the expression of an endogenous gene encoding a polypeptide of the present invention. The constructs may contain the minimal number of components necessary for altering expression of the endogenous gene. In one embodiment, the nucleic acid constructs preferably contain (a) a targeting sequence, (b) a regulatory sequence, (c) an exon, and (d) a splice-donor site. Upon introduction of the nucleic acid construct into a cell, the construct inserts by homologous recombination into the cellular genome at the endogenous gene site. The targeting sequence directs the integration of elements (a)–(d) into the endogenous gene such that elements (b)–(d) are operably linked to the endogenous gene. In another embodiment, the nucleic acid constructs contain (a) a targeting sequence, (b) a regulatory sequence, (c) an exon, (d) a splice-donor site, (e) an intron, and (f) a splice-acceptor site, wherein the targeting sequence directs the integration of elements (a)–(f) such that elements (b)–(f) are operably linked to the endogenous gene. However, the constructs may contain additional components such as a selectable marker.

In both embodiments, the introduction of these components results in production of a new transcription unit in which expression of the endogenous gene is altered. In essence, the new transcription unit is a fusion product of the sequences introduced by the targeting constructs and the endogenous gene. In one embodiment in which the endogenous gene is altered, the gene is activated. In this embodiment, homologous recombination is used to replace, disrupt, or disable the regulatory region normally associated with the endogenous gene of a parent cell through the insertion of a regulatory sequence which causes the gene to be expressed at higher levels than evident in the corresponding parent cell. The activated gene can be further amplified by the inclusion of an amplifiable selectable marker gene in the construct using methods well known in the art (see, for example, U.S. Pat. No. 5,641,670). In another embodiment in which the endogenous gene is altered, expression of the gene is reduced.

The targeting sequence can be within the endogenous gene, immediately adjacent to the gene, within an upstream gene, or upstream of and at a distance from the endogenous gene. One or more targeting sequences can be used. For example, a circular plasmid or DNA fragment preferably employs a single targeting sequence, while a linear plasmid or DNA fragment preferably employs two targeting sequences.

The regulatory sequence of the construct can be comprised of one or more promoters, enhancers, scaffold-attachment regions or matrix attachment sites, negative regulatory elements, transcription binding sites, or combinations of these sequences.

The constructs further contain one or more exons of the endogenous gene. An exon is defined as a DNA sequence which is copied into RNA and is present in a mature mRNA molecule such that the exon sequence is in-frame with the coding region of the endogenous gene. The exons can, optionally, contain DNA which encodes one or more amino acids and/or partially encodes an amino acid. Alternatively, the exon contains DNA which corresponds to a 5' non-encoding region. Where the exogenous exon or exons encode one or more amino acids and/or a portion of an amino acid, the nucleic acid construct is designed such that, upon transcription and splicing, the reading frame is in-frame with the coding region of the endogenous gene so that the appropriate reading frame of the portion of the mRNA derived from the second exon is unchanged.

The splice-donor site of the constructs directs the splicing of one exon to another exon. Typically, the first exon lies 5' of the second exon, and the splice-donor site overlapping and flanking the first exon on its 3' side recognizes a splice-acceptor site flanking the second exon on the 5' side of the second exon. A splice-acceptor site, like a splice-donor site, is a sequence which directs the splicing of one exon to another exon. Acting in conjunction with a splice-donor site, the splicing apparatus uses a splice-acceptor site to effect the removal of an intron.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the nucleic acid sequence encoding the polypeptide or any other element of the vector for integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. Examples of origins of replication for use in a yeast host cell are the 2 micron origin of replication, ARS1, ARS4, the combination of ARS 1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433). More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular cells are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*; or a *Streptomyces* cell, e.g., *Streptomyces lividans* and *Streptomyces murinus*, or gram negative bacteria such as *E. coli* and *Pseudomonas* sp. In a preferred embodiment, the bacterial host cell is a *Bacillus lentus, Bacillus licheniformis, Bacillus stearothermophilus*, or *Bacillus subtilis* cell. In another preferred embodiment, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111–115), using competent cells (see, e.g., Young and Spizizin, 1961, *Journal of Bacteriology* 81: 823–829, or Dubnau and Davidoff-Abelson, 1971, *Journal of Molecular Biology* 56: 209–221), electroporation (see, e.g., Shigekawa and Dower, 1988, *Biotechniques* 6: 742–751), or conjugation (see, e.g., Koehler and Thorne, 1987, *Journal of Bacteriology* 169: 5771–5278).

The host cell may be a eukaryote, such as a mammalian, insect, plant, or fungal cell.

In a preferred embodiment, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred embodiment, the yeast host cell is a *Candida, Hansenula, Kluyveromyces, Pichia, Saccharomyces, Schizosaccharomyces*, or *Yarrowia* cell.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal host cell is a cell of a species of, but not limited to, *Acremonium, Aspergillus, Fusarium, Humicola, Mucor, Myceliophthora, Neurospora, Penicillium, Thielavia, Tolypocladium*, or *Trichoderma*.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In an even most preferred embodiment, the filamentous fungal parent cell is a *Fusarium venenatum* (Nirenberg sp. nov.) cell. In another most preferred embodiment, the filamentous fungal host cell is a *Humicola insolens, Humicola lanuginosa, Mucor mie-* hei, *Myceliophthora thermophila, Neurospora crassa, Penicillium purpurogenum, Thielavia terrestris, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470–1474. Suitable methods for transforming *Fusarium* species are described by Malardier et al., 1989, *Gene* 78: 147–156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182–187, Academic Press, Inc., New York; Ito et al., 1983, *Journal of Bacteriology* 153: 163; and Hinnen et al., 1978, *Proceedings of the National Academy ofsciences USA* 75: 1920.

Methods of Production

The present invention also relates to methods for producing a polypeptide of the present invention comprising (a) cultivating a strain, which in its wild-type form is capable of producing the polypeptide, to produce a supernatant comprising the polypeptide; and (b) recovering the polypeptide. Preferably, the strain is of the genus *Aspergillus*, and more preferably *Aspergillus oryzae*.

The present invention also relates to methods for producing a polypeptide of the present invention comprising (a) cultivating a host cell under conditions conducive for production of the polypeptide; and (b) recovering the polypeptide.

The present invention also relates to methods for producing a polypeptide of the present invention comprising (a) cultivating a host cell under conditions conducive for production of the polypeptide, wherein the host cell comprises a mutant nucleic acid sequence having at least one mutation in the mature polypeptide coding region of SEQ ID NO. 1, wherein the mutant nucleic acid sequence encodes a polypeptide which consists of amino acids 20 to 464 of SEQ ID NO. 2, and (b) recovering the polypeptide.

The present invention further relates to methods for producing a polypeptide of the present invention comprising (a) cultivating a homologously recombinant cell, having incorporated therein a new transcription unit comprising a regulatory sequence, an exon, and/or a splice donor site operably linked to a second exon of an endogenous nucleic acid sequence encoding the polypeptide, under conditions conducive for production of the polypeptide; and (b) recovering the polypeptide. The methods are based on the use of gene activation technology, for example, as described in U.S. Pat. No. 5,641,670.

In the production methods of the present invention, the cells are cultivated in a nutrient medium suitable for production of the polypeptide using methods known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Plants

The present invention also relates to a transgenic plant, plant part, or plant cell which has been transformed with a nucleic acid sequence encoding a polypeptide having phospholipase B activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as festuca, lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers. Also specific plant tissues, such as chloroplast, apoplast, mitochondria, vacuole, peroxisomes, and cytoplasm are considered to be a plant part. Furthermore, any plant cell, whatever the tissue origin, is considered to be a plant part.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleic acid sequence encoding a polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al, 1988, *Plant Physiology* 86: 506.

For constitutive expression, the 35S-CaMV promoter may be used (Franck et al., 1980, *Cell* 21: 285–294). Organ-specific promoters may be, for example, a promoter from storage sink tissues such as seeds, potato tubers, and fruits (Edwards & Coruzzi, 1990, *Ann. Rev. Genet.* 24: 275–303), or from metabolic sink tissues such as meristems (Ito et al., 1994, *Plant Mol. Biol.* 24: 863–878), a seed specific promoter such as the glutelin, prolamin, globulin, or albumin promoter from rice (Wu et al., 1998, *Plant and Cell Physiology* 39: 885–889), a Viciafaba promoter from the legumin B4 and the unknown seed protein gene from Viciafaba (Conrad et al., 1998, *Journal of Plant Physiology* 152: 708–711), a promoter from a seed oil body protein (Chen et al., 1998, *Plant and Cell Physiology* 39: 935–941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991–1000, the chlorella virus adenine methyltransferase gene promoter (Mitra and Higgins, 1994, *Plant Molecular Biology* 26: 85–93), or the aldP gene promoter from rice (Kagaya et al., 1995, *Molecular and General Genetics* 248: 668–674), or a wound inducible promoter such as the potato pin2 promoter (Xu et al., 1993, *Plant Molecular Biology* 22: 573–588).

A promoter enhancer element may also be used to achieve higher expression of the enzyme in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8:535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15–38). However it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275–281; Shimamoto, 1994, *Current Opinion Biotechnology* 5: 158–162; Vasil et al., 1992, *Bio/Technology* 10: 667–674). An alternative method for transformation of monocots is based on protoplast transformation as described by Omirulleh et al., 1993, *Plant Molecular Biology* 21: 415428.

Following transformation, the transformants having incorporated therein the expression construct are selected and regenerated into whole plants according to methods well-known in the art.

The present invention also relates to methods for producing a polypeptide of the present invention comprising (a) cultivating a transgenic plant or a plant cell comprising a nucleic acid sequence encoding a polypeptide having phospholipase B activity of the present invention under conditions conducive for production of the polypeptide; and (b) recovering the polypeptide.

Removal or Reduction of Phospholipase B Activity

The present invention also relates to methods for producing a mutant cell of a parent cell, which comprises disrupting or deleting a nucleic acid sequence encoding the polypeptide or a control sequence thereof, which results in the mutant cell producing less of the polypeptide than the parent cell when cultivated under the same conditions.

The construction of strains which have reduced phospholipase B activity may be conveniently accomplished by modification or inactivation of a nucleic acid sequence necessary for expression of the polypeptide having phospholipase B activity in the cell. The nucleic acid sequence to be modified or inactivated may be, for example, a nucleic acid sequence encoding the polypeptide or a part thereof essential for exhibiting phospholipase B activity, or the nucleic acid sequence may have a regulatory function required for the expression of the polypeptide from the coding sequence of the nucleic acid sequence. An example of such a regulatory or control sequence may be a promoter sequence or a functional part thereof, i.e., a part which is sufficient for affecting expression of the polypeptide. Other control sequences for possible modification are described above.

Modification or inactivation of the nucleic acid sequence may be performed by subjecting the cell to mutagenesis and selecting or screening for cells in which the phospholipase B producing capability has been reduced. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the cell to be mutagenized in the presence of the mutagenizing agent of choice under suitable conditions, and selecting for cells exhibiting reduced phospholipase B activity or production.

Modification or inactivation of production of a polypeptide of the present invention may be accomplished by introduction, substitution, or removal of one or more nucleotides in the nucleic acid sequence encoding the polypeptide or a regulatory element required for the transcription or translation thereof. For example, nucleotides may be inserted or removed so as to result in the introduction of a stop codon, the removal of the start codon, or a change of the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleic acid sequence to be modified, it is preferred that the modification be performed in vitro as exemplified below.

An example of a convenient way to eliminate or reduce production by a host cell of choice is by gene replacement or gene interruption. In the gene interruption method, a nucleic acid sequence corresponding to the endogenous gene or gene fragment of interest is mutagenized in vitro to produce a defective nucleic acid sequence which is then transformed into the host cell to produce a defective gene. By homologous recombination, the defective nucleic acid sequence replaces the endogenous gene or gene fragment. It may be desirable that the defective gene or gene fragment also encodes a marker which may be used for selection of transformants in which the gene encoding the polypeptide has been modified or destroyed.

Alternatively, modification or inactivation of the nucleic acid sequence may be performed by established anti-sense techniques using a nucleotide sequence complementary to the polypeptide encoding sequence. More specifically, production of the polypeptide by a cell may be reduced or eliminated by introducing a nucleotide sequence complementary to the nucleic acid sequence encoding the polypeptide which may be transcribed in the cell and is capable of hybridizing to the polypeptide mRNA produced in the cell. Under conditions allowing the complementary anti-sense nucleotide sequence to hybridize to the polypeptide mRNA, the amount of polypeptide translated is thus reduced or eliminated.

It is preferred that the cell to be modified in accordance with the methods of the present invention is of microbial origin, for example, a fungal strain which is suitable for the production of desired protein products, either homologous or heterologous to the cell.

The present invention further relates to a mutant cell of a parent cell which comprises a disruption or deletion of a nucleic acid sequence encoding the polypeptide or a control sequence thereof, which results in the mutant cell producing less of the polypeptide than the parent cell.

The polypeptide-deficient mutant cells so created are particularly useful as host cells for the expression of homologous and/or heterologous polypeptides. Therefore, the present invention further relates to methods for producing a homologous or heterologous polypeptide comprising (a) cultivating the mutant cell under conditions conducive for production of the polypeptide; and (b) recovering the polypeptide. The term "heterologous polypeptides" is defined herein as polypeptides which are not native to the host cell, a native protein in which modifications have been made to alter the native sequence, or a native protein whose expression is quantitatively altered as a result of a manipulation of the host cell by recombinant DNA techniques.

In a further aspect, the present invention relates to a method for producing a protein product essentially free of phospholipase B activity by fermentation of a cell which produces both a polypeptide of the present invention as well as the protein product of interest by adding an effective amount of an agent capable of inhibiting phospholipase B activity to the fermentation broth before, during, or after the fermentation has been completed, recovering the product of interest from the fermentation broth, and optionally subjecting the recovered product to further purification.

In a further aspect, the present invention relates to a method for producing a protein product essentially free of phospholipase B activity by cultivating the cell under conditions permitting the expression of the product, subjecting the resultant culture broth to a combined pH and temperature treatment so as to reduce the phospholipase B activity substantially, and recovering the product from the culture broth. Alternatively, the combined pH and temperature treatment may be performed on an enzyme preparation recovered from the culture broth. The combined pH and temperature treatment may optionally be used in combination with a treatment with a phospholipase B inhibitor.

In accordance with this aspect of the invention, it is possible to remove at least 60%, preferably at least 75%, more preferably at least 85%, still more preferably at least 95%, and most preferably at least 99% of the phospholipase B activity. Complete removal of phospholipase B activity may be obtained by use of this method.

The combined pH and temperature treatment is preferably carried out at a pH in the range of 6.5–8.0 and a temperature in the range of 45–70° C. for a sufficient period of time to attain the desired effect, where typically, 30 to 60 minutes is sufficient.

The methods used for cultivation and purification of the product of interest may be performed by methods known in the art.

The methods of the present invention for producing an essentially phospholipase B-free product is of particular interest in the production of eukaryotic polypeptides, in particular fungal proteins such as enzymes. The enzyme may be selected from, e.g., an amylolytic enzyme, lipolytic enzyme, proteolytic enzyme, cellulytic enzyme, oxidoreductase, or plant cell-wall degrading enzyme. Examples of such enzymes include an aminopeptidase, amylase, amyloglucosidase, carbohydrase, carboxypeptidase, catalase, cellulase, chitinase, cutinase, cyclodextrin glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or xylanase. The phospholipase B-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from phospholipase B activity which is produced by a method of the present invention.

Compositions

In a still further aspect, the present invention relates to compositions comprising a polypeptide of the present invention. Preferably, the compositions are enriched in a polypeptide of the present invention. In the present context, the term "enriched" indicates that the phospholipase B activity of the composition has been increased, e.g., with an enrichment factor of 1.1.

The composition may comprise a polypeptide of the invention as the major enzymatic component, e.g., a monocomponent composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced by means of a microorganism belonging to the genus *Aspergillus*, preferably *Aspergillus aculeatus, Aspergillus awamori, Aspergillus niger*, or *Aspergillus oryzae*, or *Trichoderma, Humicola*, preferably *Humicola insolens*, or *Fusarium*, preferably *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides*, or *Fusarium venenatum*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention is also directed to methods for using the polypeptides having phospholipase activity.

The polypeptides of the present invention may be used in any application where it is desired to hydrolyze the fatty acyl group(s) of a phospholipid or lysophospholipid, such as lecithin or lysolecithin. The polypeptides of the present invention are preferably used at a pH optimal for activity.

A polypeptide of the present invention may be used for deguming an aqueous carbohydrate solution or slurry to improve its filterability, particularly, a starch hydrolysate, especially a wheat starch hydrolysate which is difficult to filter and yields cloudy filtrates. The treatment may be performed using methods well known in the art. See, for example, EP 219,269 and EP 808,903.

A polypeptide of the present invention may be used in a process to reduce the phospholipid content in an edible oil by treating the oil with the polypeptide to hydrolyze a major portion of the phospholipid and separating an aqueous phase containing the hydrolyzed phospholipid from the oil. Such a process is applicable to the purification of any edible oil which contains phospholipid, e.g., vegetable oil such as soybean oil, rape seed oil, and sunflower oil.

Prior to the phospholipase treatment, the oil is preferably pretreated to remove slime (mucilage), e.g., by wet refining. Typically, the oil will contain 50–250 ppm of phosphorus as phospholipid at the beginning of the treatment with the phospholipase, and the treatment may reduce the phosphorus value to below 5–10 ppm.

The phospholipase treatment is conducted by dispersing an aqueous solution of the phospholipase, preferably as droplets with an average diameter below 10 μm. The amount of water is preferably 0.5–5% by weight in relation to the oil. An emulsifier may optionally be added. Mechanical agitation may be applied to maintain the emulsion.

The phospholipase treatment can be conducted at a pH in the range of about 1.5 to about 5.0. The process pH may be in the range of about 3.5 to about 5 to maximize the enzyme's performance, or a pH in the range of about 1.5 to about 3 (e.g., 2–3) may be used in order to suppress the alkaline hydrolysis of triglycerides (saponification). The pH may be adjusted by adding citric acid, a citrate buffer, or hydrochloric acid.

A suitable temperature is generally 30–70° C. (particularly 30–45° C., e.g., 35–40° C.). The reaction time will typically be 1–12 hours (e.g., 2–6 hours). A suitable enzyme dosage will usually be 0.1–10 mg per liter (e.g., 0.5–5 mg per liter).

The phospholipase treatment may be conducted batchwise, e.g., in a tank with stirring, or it may be continuous, e.g., a series of stirred tank reactors.

The phospholipase treatment is followed by separation of an aqueous phase and an oil phase. The separation may be performed by conventional means, e.g., centrifugation. The aqueous phase will contain phospholipase, and the enzyme may be re-used to improve the process economy.

The treatment may be performed using any of the methods known in the art. See, for example, U.S. Pat. No. 5,264,367, EP 654,527, JP-A 2-153997.

The present invention also relates to methods for preparing a dough or a baked product comprising incorporating into the dough an effective amount of a polypeptide of the present invention which improves one or more properties of the dough or the baked product obtained from the dough relative to a dough or a baked product in which the polypeptide is not incorporated.

The phrase "incorporating into the dough" is defined herein as adding the phospholipase B to the dough, any ingredient from which the dough is to be made, and/or any mixture of dough ingredients from which the dough is to be made. In other words, the phospholipase B may be added in any step of the dough preparation and may be added in one, two, or more steps. The phospholipase B is added to the ingredients of a dough which is kneaded and baked to make the baked product using methods well known in the art. See, for example, U.S. Pat. No. 4,567,046, EP 426,211, JP-A 60-78529, JP-A 62-111629, and JP-A 63-258528.

The term "effective amount" is defined herein as an amount of the phospholipase B that is sufficient for providing a measurable effect on at least one property of interest of the dough and/or baked product.

The term "improved property" is defined herein as any property of a dough and/or a product obtained from the dough, particularly a baked product, which is improved by the action of the phospholipase B relative to a dough or product in which the phospholipase B is not incorporated. The improved property may include, but is not limited to, increased strength of the dough, increased elasticity of the dough, increased stability of the dough, reduced stickiness of the dough, improved extensibility of the dough, improved machinability of the dough, increased volume of the baked product, improved crumb structure of the baked product, improved softness of the baked product, improved flavor of the baked product, and/or improved antistaling of the baked product.

The improved property may be determined by comparison of a dough and/or a baked product prepared with and without addition of a polypeptide having phospholipase B activity of the present invention in accordance with the methods of the present invention. Techniques which can be used to determine improvements achieved by use of the methods of present invention are described below in the Examples. Organoleptic qualities may be evaluated using procedures well established in the baking industry, and may include, for example, the use of a panel of trained taste-testers.

The term "increased strength of the dough" is defined herein as the property of a dough that has generally more elastic properties and/or requires more work input to mould and shape.

The term "increased elasticity of the dough" is defined herein as the property of a dough which has a higher tendency to regain its original shape after being subjected to a certain physical strain.

The term "increased stability of the dough" is defined herein as the property of a dough that is less susceptible to mechanical abuse thus better maintaining its shape and volume.

The term "reduced stickiness of the dough" is defined herein as the property of a dough that has less tendency to adhere to surfaces, e.g., in the dough production machinery, and is either evaluated empirically by the skilled test baker or measured by the use of a texture analyzer (e.g., TAXT2) as known in the art.

The term "improved extensibility of the dough" is defined herein as the property of a dough that can be subjected to increased strain or stretching without rupture.

The term "improved machinability of the dough" is defined herein as the property of a dough that is generally less sticky and/or more firm and/or more elastic.

The term "increased volume of the baked product" is measured as the specific volume of a given loaf of bread (volume/weight) determined typically by the traditional rape seed displacement method.

The term "improved crumb structure of the baked product" is defined herein as the property of a baked product with finer and/or thinner cell walls in the crumb and/or more uniform/homogenous distribution of cells in the crumb and is usually evaluated empirically by the skilled test baker.

The term "improved softness of the baked product" is the opposite of "firmness" and is defined herein as the property of a baked product that is more easily compressed and is evaluated either empirically by the skilled test baker or measured by the use of a texture analyzer (e.g., TAXT2) as known in the art.

The term "improved flavor of the baked product" is evaluated by a trained test panel.

The term "improved antistaling of the baked product" is defined herein as the properties of a baked product that have a reduced rate of deterioration of quality parameters, e.g., softness and/or elasticity, during storage.

The term "dough" is defined herein as a mixture of flour and other ingredients firm enough to knead or roll. The dough may be fresh, frozen, pre-bared, or pre-baked. The preparation of frozen dough is described by Kulp and Lorenz in *Frozen and Refrigerated Doughs and Batters*.

The term "baked product" is defined herein as any product prepared from a dough, either of a soft or a crisp character. Examples of baked products, whether of a white, light or dark type, which may be advantageously produced by the present invention are bread (in particular white, whole-meal or rye bread), typically in the form of loaves or rolls, French baguette-type bread, pasta, pita bread, tortillas, tacos, cakes, pancakes, biscuits, cookies, pie crusts, steamed bread, and crisp bread, and the like.

The polypeptide having phospholipase B activity and/or additional enzymes to be used in the methods of the present invention may be in any form suitable for the use in question, e.g., in the form of a dry powder, agglomerated powder, or granulate, in particular a non-dusting granulate, liquid, in particular a stabilized liquid, or protected enzyme. Granulates and agglomerated powders may be prepared by conventional methods, e.g., by spraying the phospholipase B onto a carrier in a fluid-bed granulator. The carrier may consist of particulate cores having a suitable particle size. The carrier may be soluble or insoluble, e.g., a salt (such as NaCl or sodium sulfate), sugar (such as sucrose or lactose), sugar alcohol (such as sorbitol), starch, rice, corn grits, or soy. The phospholipase B and/or additional enzymes may be contained in slow-release formulations. Methods for preparing slow-release formulations are well known in the art. Liquid enzyme preparations may, for instance, be stabilized by adding nutritionally acceptable stabilizers such as a sugar, sugar alcohol, or another polyol, and/or lactic acid or another organic acid according to established methods.

For inclusion in pre-mixes or flour it is advantageous that the polypeptide having phospholipase B activity is in the form of a dry product, e.g., a non-dusting granulate, whereas for inclusion together with a liquid it is advantageously in a liquid form.

One or more additional enzymes may also be incorporated into the dough. The additional enzyme may be of any origin, including mammalian and plant, and preferably of microbial (bacterial, yeast or fungal) origin and may be obtained by techniques conventionally used in the art.

In a preferred embodiment, the additional enzyme may be an amylase, such as an alpha-amylase (useful for providing sugars fermentable by yeast and retarding staling) or beta-amylase, cyclodextrin glucanotransferase, peptidase, in particular, an exopeptidase (useful in flavour enhancement), transglutaminase, lipase (useful for the modification of lipids present in the dough or dough constituents so as to soften the dough), phospholipase (useful for the modification of lipids present in the dough or dough constituents so as to soften the dough and improve gas retention in the dough), cellulase, hemicellulase, in particular a pentosanase such as xylanase (useful for the partial hydrolysis of pentosans which increases the extensibility of the dough), protease (useful for gluten weakening in particular when using hard wheat flour), protein disulfide isomerase, e.g., a protein disulfide isomerase as disclosed in WO 95/00636, glycosyltransferase, peroxidase (useful for improving the dough consistency), laccase, or oxidase, e.g., an aldose oxidase, glucose oxidase, pyranose oxidase, lipoxygenase, or L-amino acid oxidase (useful in improving dough consistency).

When one or more additional enzyme activities are to be added in accordance with the methods of the present invention, these activities may be added separately or together with the polypeptide having phospholipase B activity, optionally as constituent(s) of the bread-improving and/or dough-improving composition. The other enzyme activities may be any of the enzymes described above and may be dosed in accordance with established baking practices.

The present invention also relates to methods for preparing a baked product, comprising baking a dough obtained by a method of the present invention to produce a baked product. The baking of the dough to produce a baked product may be performed using methods well known in the art.

The present invention also relates to doughs and baked products, respectively, produced by the methods of the present invention.

The present invention further relates to a pre-mix, e.g., in the form of a flour composition, for dough and/or baked products made from dough, in which the pre-mix comprises a polypeptide having phospholipase B activity of the present invention. The term "pre-mix" is defined herein to be understood in its conventional meaning, i.e., as a mix of baking agents, generally including flour, which may be used not only in industrial bread-baking plants/facilities, but also in retail bakeries. The pre-mix may be prepared by mixing the polypeptide or a bread-improving and/or dough-improving composition of the invention comprising the polypeptide with a suitable carrier such as flour, starch, a sugar, or a salt. The pre-mix may contain other dough-improving and/or bread-improving additives, e.g., any of the additives, including enzymes, mentioned above.

The present invention further relates to baking additives in the form of a granulate or agglomerated powder, which comprise a polypeptide having phospholipase B activity of the present invention. The baking additive preferably has a narrow particle size distribution with more than 95% (by weight) of the particles in the range from 25 to 500 µm;

Signal Peptide

The present invention also relates to nucleic acid constructs comprising a gene encoding a protein operably linked to a nucleic acid sequence consisting of nucleotides 510 to 567 of SEQ ID NO. 1 encoding a signal peptide consisting of amino acids 1 to 19 of SEQ ID NO. 2, wherein the gene is foreign to the nucleic acid sequence.

The present invention also relates to recombinant expression vectors and recombinant host cells comprising such a nucleic acid construct.

The present invention also relates to methods for producing a protein comprising (a) cultivating such a recombinant host cell under conditions suitable for production of the protein; and (b) recovering the protein.

The nucleic acid sequence may be operably linked to foreign genes with other control sequences. Such other control sequences are described above.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides which comprise a combination of partial or complete polypeptide sequences obtained from at least two different proteins wherein one or more may be heterologous or native to the host cell. Proteins further include naturally occurring allelic and engineered variations of the above mentioned proteins and hybrid proteins.

Preferably, the protein is a hormone, hormone variant, enzyme, receptor or a portion thereof, antibody or a portion thereof, or reporter. In a more preferred embodiment, the protein is an oxidoreductase, transferase, hydrolase, lyase, isomerase, or ligase. In an even more preferred embodiment, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, pectolytic enzyme, peroxidase, phytase, polyphenoloxidase, proteolytic enzyme, ribonuclease, transglutaminase, or xylanase.

The gene may be obtained from any prokaryotic, eukaryotic, or other source. For purposes of the present invention, the term "obtained from" as used herein in connection with a given source shall mean that the protein is produced by the source or by a cell in which a gene from the source has been inserted.

The present invention is further described by the following examples which should not be construed as limiting the scope of the invention.

EXAMPLES

Chemicals used as buffers and substrates were commercial products of at least reagent grade.

Example 1

*Aspergillus oryzae* Genomic DNA Extraction

*Aspergillus oryzae* HowB430 (WO 98/11203) was grown in 25 ml of 0.5% yeast extract-2% glucose (YEG) medium for 24 hours at 37° C. and 250 rpm. Mycelia were then collected by filtration through Miracloth (Calbiochem, La Jolla, Calif.) and washed once with 25 ml of 10 mM Tris-1 mM EDTA (TE) buffer. Excess buffer was drained from the mycelia preparation which was subsequently frozen in liquid nitrogen. The frozen mycelia preparation was ground to a fine powder in an electric coffee grinder, and the powder was added to a disposable plastic centrifuge tube containing 20 ml of TE buffer and 5 ml of 20% w/v sodium dodecylsulfate (SDS). The mixture was gently inverted several times to ensure mixing, and extracted twice with an equal volume of phenol:chloroform:isoamyl alcohol (25:24:1 v/v/v). Sodium acetate (3 M solution) was added to the extracted sample to a final concentration of 0.3 M followed by 2.5 volumes of ice cold ethanol to precipitate the DNA. The tube was centrifuged at 15,000×g for 30 minutes to pellet the DNA. The DNA pellet was allowed to air-dry for 30 minutes before resuspension in 0.5 ml of TE buffer. DNase-free ribonuclease A was added to the resuspended DNA pellet to a concentration of 100 µg per ml and the mixture was then incubated at 37° C. for 30 minutes. Proteinase K (200 µg/ml) was added and the tube was incubated an additional one hour at 37° C. Finally, the sample was extracted twice with phenol:chloroform:isoamyl alcohol and the DNA precipitated with ethanol. The precipitated DNA was washed with 70% ethanol, dried under vacuum, resuspended in TE buffer, and stored at 4° C.

Example 2

DNA Libraries and Identification of *Aspergillus oryzae* Phospholipase B Clones

Genomic DNA libraries were constructed using the bacteriophage cloning vector λZipLox (Life Technologies, Gaithersburg, Md.) with *E. coli* Y1090ZL cells (Life Technologies, Gaithersburg, Md.) as a host for plating and purification of recombinant bacteriophage and *E. coli* DH10Bzip (Life Technologies, Gaithersburg, Md.) for excision of individual pZL1 clones containing the phospholipase B gene.

*Aspergillus oryzae* HowB430 genomic DNA was partially digested with Tsp509I and size-fractionated on 1% agarose gels. DNA fragments migrating in the size range 3–7 kb were excised and eluted from the gel using Prep-a-Gene reagents (BioRad Laboratories, Hercules, Calif.). The eluted DNA fragments were ligated with EcoRI-cleaved and dephosphorylated XZipLox vector arms (Life Technologies, Gaithersburg, Md.), and the ligation mixtures were packaged using commercial packaging extracts (Stratagene, La Jolla, Calif.). The packaged DNA libraries were plated and amplified in *Escherichia coli* Y1090ZL cells (Life Technologies, Gaithersburg, Md.).

A genomic clone designated clone 10.2 #10 was inoculated into three ml of LB plus 50 µg/ml ampicillin medium and grown overnight at 37° C. Miniprep DNA was prepared from this clone using the Bio Robot 9600 (Qiagen Inc., Valencia, Calif.) according to the manufacturer's protocol. The clone was determined by DNA sequencing to contain a portion of a phospholipase B gene. DNA sequencing of each clone was performed with an Applied Biosystems Prism 377 DNA Sequencer using the BigDye Terminator Cycle Sequencing Ready Reaction kit (Applied Biosystems, Inc., Foster City, Calif.) according to the manufacturer's instructions.

In order to recover additional sequence, a XhoI/SalI fragment from the insert in this clone was used to probe the same genomic library.

The *Aspergillus oryzae* HowB430 DNA library was plated on NZCYM agar plates. Plaque lifts (Maniatis et al., 1982, *Molecular Cloning, A Laboratory Manual*, Cold Spring Harbor Press, Cold Spring Harbor, N.Y.) were performed on approximately 40,000 colonies and the DNA was fixed onto membranes by heating at 80° C. for two hours. The membranes were soaked for 30 minutes at 65° C. in a hybridization solution containing 6×SSPE and 7.0% SDS. The phospholipase B gene fragment isolated from the *Aspergillus oryzae* HowB430 as described above was radiolabeled using the Prime-It II Random Primer Labeling Kit (Stratagene, La Jolla, Calif.), denatured by adding NaOH to a final concentration of 0.5 M, and added to the hybridization solution at an activity of approximately $1 \times 10^6$ cpm per ml of hybridization solution. The mixture was incubated overnight at 65° C. in a shaking water bath. Following incubation, the membranes were washed four times in 0.2×SSC with 0.2% SDS at 65° C. The membranes were then dried on blotting paper for 15 minutes, wrapped in SaranWrap™, and exposed to X-ray film for 48 hours at −80° C. with intensifying screens (Kodak, Rochester, N.Y.).

Eleven plaques, designated clones 12, 14, 15, 16, 18, 20, 21, 22, 23, 26, and 27, produced strong hybridization signals with the probe. These were plaque purified and the pZL1 plasmids were excised from the purified phagemid clones according to the protocol suggested by Life Technologies (Gaithersburg, Md.). Colonies were inoculated into three ml of LB plus 50 µg/ml ampicillin medium and grown overnight at 37° C. Miniprep DNA was prepared from each of these clones using the Qiagen Bio Robot 9600 according to the manufacturer's protocol.

DNA sequencing of each clone was performed with an Applied Biosystems Prism 377 DNA Sequencer using the BigDye Terminator Cycle Sequencing Ready Reaction kit according to the manufacturer's instructions. Oligonucleotide sequencing primers were designed to complementary sequences in the pZL1 plasmid vector and were synthesized by Operon Technologies Inc., Alameda, Calif.

DNA sequencing indicated that the eleven clones contained all of the phospholipase B coding sequence (FIG. 1). The region spanned by clones 16, 20, 23 and 27 was sequenced to an average redundancy of 5.

Example 3

PCR Amplification of *Aspergillus oryzae* Phospholipase B Gene

The complete phospholipase B coding sequence was amplified by PCR from clone 16.1 #22 using the Expand High Fidelity PCR kit (Roche Molecular Biochemicals, Indianapolis, Ind.) according to the manufacturer's suggested protocol using the following primers which incorporated SwaI or PacI cloning sites:

Sense primer: 5'-ATTTAAATGATGAAGTCCAC-CGCTCTG-3' (SEQ ID NO. 3)

Antisense primer: 5'-GTTAATTAAACTTATAC-CGAAAAGGTATGG-3' (SEQ ID NO. 4)

Amplification reactions (50 µl) were prepared using approximately 0.2 µg of heat-denatured plasmid DNA as the template. Each reaction contained the following components: 0.2 µg of heat-denatured plasmid DNA, 15 pmol of the forward primer, 15 pmol of the reverse primer, 250 µM each of DATP, dCTP, dGTP, and dTTP, 1× buffer, and 3.5 units of DNA polymerase mixture (Taq and Pwo DNA polymerases). The reactions were incubated in a Strategene RoboCycler programmed for 12 cycles each at 94° C. for 45 seconds, 55° C. (first cycle) or 57° C. for 30 seconds, 72° C. for 120 seconds, and 72° C. post-cycle for 5 minutes.

The reaction products were isolated on a 0.8% agarose gel using TAE buffer where a 1.6 kb product band was excised from the gel and purified using a QIAquick kit (QIAGEN, Chatsworth, Calif.) according to the manufacturer's instructions. The 1.6 kb fragment was cloned into pCR®2.1 TOPO (Invitrogen, San Diego, Calif.) after addition of 3' A-overhangs according to the manufacturer's suggested protocol. The insert from one selected clone was removed by sequential digestion with PacI and SwaI, gel purified, and ligated into similarly digested pBANe15. The ligation mixture was cloned into *E. coli* DH5α cells to produce *E. coli* DH5α pPH6. The resulting plasmid containing the full-length phospholipase B gene was designated pPH6.

Example 4

DNA Sequence Analysis of *Aspergillus oryzae* Phospholipase B Gene

DNA sequencing of the phospholipase B gene contained in pPH6 of *E. coli* DH5α pPH6 was performed as described in Example 2 using M13 reverse and T7 oligonucleotide sequencing primers (Operon Technologies, Inc).

The nucleotide sequence of the gene encoding the *Aspergillus oryzae* HowB430 phospholipase B and the deduced amino acid sequence thereof is shown in FIG. 1 (SEQ ID NOs. 1 and 2, respectively). Sequence analysis of the cloned insert revealed a coding sequence of 1392 bp (excluding the stop codon) encoding a protein of 464 amino acids sequence (SEQ ID NO. 2). The coding sequence is punctuated by two introns of 92 bp and 51 bp. The G+C content of the coding sequence is 55.3%. The predicted mature phospholipase B polypeptide has a molecular mass of 49.4 kdal and an isoelectric point of 4.76. Based on the rules of van Heijne (van Heijne, 1984, *Journal of Molecular Biology* 173: 243–251), the first 19 amino acids likely comprise a secretory signal peptide which directs the nascent polypeptide into the endoplasmic reticulum.

A comparative multiple alignment of phospholipase B polypeptide sequences was determined by the ClustalW method using the ClustalX software (Thompson et al., 1994, *Nucleic Acids Research* 22: 4673–4680; Thompson et al., 1997, *Nucleic Acids Research* 25: 4876–4882) with a blosum weight matrix, gap opening penalty of 10, and gap extension penalty of 0.03 to 0.05. The comparative alignment showed that the *Aspergillus oryzae* HowB430 phospholipase B shares 26% identity with a phospholipase C from *Pseudomonas aeruginosa* (SwissProt Acc. No. P15713).

Example 5

Expression of *Aspergillus oryzae* Phospholipase B in *Aspergillus oryzae*

Plasmid pPH6 was digested with PmeI to isolate the phospholipase B expression cassette, which was purified by agarose gel electrophoresis and recovered using the QIAquick kit.

The purified fragment was transformed into *Aspergillus oryzae* strain BECh2 (Δalp, ΔnpI) using the following protoplast transformation method. Protoplasts of *Aspergillus oryzae* strain BECh2 were prepared according to the method of Christensen et al., 1988, *Bio/Technology* 6: 1419–1422. The transformation was conducted with protoplasts at a concentration of ca. $2 \times 10^7$ protoplasts per ml. One hundred μl of protoplasts were placed on ice for 5 minutes with ca. 2.5 μg of the PmeI fragment; 250 μl of 60% polyethylene glycol 4000, 10 mM Tris-HCl, pH 7.5, 10 mM $CaCl_2$ was added, and the protoplasts were incubated at 37° C. for 30 minutes. Three mls of STC (1.2 M sorbitol, 10 mM Tris-HCl, pH 7.5, and 10 mM $CaCl_2$) was added. The solution was mixed gently and poured onto 150 mm COVE transformation plates (per liter: 0.52 g of KCl, 0.52 g of $MgSO_4$-$7H_2O$, 1.52 g of $KH2PO_4$, 1 ml of trace metals described below, 342.3 g of sucrose, 25 g of Noble agar, 10 ml of 1 M acetamide, 10 ml of 3 M CsCl). The trace metals solution (1000×) was comprised of 22 g of $ZnSO_4$-$7H_2O$, 11 g of $H_3BO_3$, 5 g of $MnCl_2$-$4H_2O$, 5 g of $FeSO_4$-$7H_2O$, 1.6 g of $CoCl_2$-$5H_2O$, 1.6 g of $(NH_4)_6Mo_7O_{24}$, and 50 g of $Na_4EDTA$ per liter. Plates were incubated 5–7 days at 34° C. until colonies appeared. Putative transformants were spore purified twice on COVE-Vogel's medium. Ultimately 18 transformants were recovered by their ability to utilize acetamide as the sole nitrogen source. All transformants were subsequently propagated on minimal medium containing 1% glycerol as carbon source.

For initial small-scale expression analysis, freshly collected spores of the transformants were inoculated in 125 ml baffled shake flasks containing 25 ml of medium composed per liter of 50 g of maltodextrin, 2 g of $MgSO_4$-$7H_2O$, 10 g of $KH_2PO_4$, 2 g of $K_2SO_4$, 2 g of citric acid, 10 g of yeast extract, 2 g of urea, 7.1 μg of $ZnSO_4$-$7H_2O$, 1.3 μg of $CuSO_4$. $5H_2O$, 0.25 μg of $NiCl_2$.$6H_2O$, 0.7 μg of $FeSO_4$.$7H_2O$, 4.3 μg of $MnSO_4H_2O$, and 1.5 μg of citric acid per liter, titrated to pH 6.0 with sodium hydroxide. The cultures were cultivated for 3–5 days at 34° C. with constant shaking at 200 rpm.

Culture supernatants from the transformants were submitted to SDS-PAGE using 8–16% Tris-Glycine SDS-PAGE gels (Novex, San Diego). A doublet band of approximately 55–65 kDa was observed in all of the supernatants.

Culture supernatants from two of the transformants were assayed for phospholipase B activity using 9 mM p-nitrophenylphosphorylcholine as substrate in 0.1 M MOPS-4 mM $CaCl_2$ pH 7.5 at 30° C. The assays showed the presence of enzyme activity toward p-nitrophenylphosphorylcholine.

The assay results showed that the transformants produced detectable phospholipase B activity.

Example 6

Purification of Recombinant Phospholipase B

A volume of 550 ml of whole culture broth obtained as described in Example 5 was centrifuged at 6000 rpm for 30 minutes. The supernatant of 140 mls was diluted with deionized water to 840 mls to a conductivity of 2.3 mS, pH 6.8. The diluted broth was then filtered through a Millipore Express 0.22 μm filter.

Q-Sepharose Big Beads (Pharmacia Biotech, Inc., Piscataway, N.J.) were loaded into an XK-26 column to a volume of approximately 80 ml of resin and pre-equilibrated with 500 ml of 20 mM sodium phosphate pH 7.0. The sample was then loaded, followed by washing with 20 mM sodium phosphate pH 7.0 until baseline absorbance at 280 nm was achieved. A 500 ml gradient was run from 0 to 0.30 M NaCl in 20 mM sodium phosphate pH 7.0 at a flow rate of 5 ml minute for 100 minutes. Fractions of 10 ml were collected and assayed using p-nitrophenyl phosphoryl choline (Sigma Chemical Co., St. Louis, Mo.) as a substrate at a concentration of 9 mM in 100 mM MOPS-4 mM $CaCl_2$ pH 7.5. Active fractions were also analyzed by SDS-PAGE using 8–16% Tris-Glycine SDS-PAGE gels. The purified phospholipase was seen as a doublet at approximately 55–65 kDa as with the crude whole broth.

Example 7

Protein Sequencing and Amino Acid Analysis of Phospholipase B

N-terminal sequencing of the whole broth and purified phospholipase B obtained as described in Example 6 was performed on an Applied Biosystems 476A Protein Sequencer (Perkin Elmer/Applied Biosystems Division, Foster City, Calif.) with on-line HPLC and liquid phase trifluoroacetic acid (TFA) delivery. The phospholipase preparations were submitted to SDS-PAGE using Novex 8–16% Tris-glycine SDS-PAGE gels according to manufacturer's suggested conditions (Novex, San Diego, Calif.). The gels were electroblotted to a PVDF membrane (Novex, San Diego, Calif.) for 2 hours at 25 volts in 10 mM CAPS pH 11.0 buffer. The PVDF membrane was stained in 0.1% Commassie Blue R250 in 40% methanol/1% acetic acid and the observed bands excised. The excised bands were sequenced from a blot cartridge using sequencing reagents (Perkin Elmer/Applied Biosystems Division, Foster City, Calif.). Detection of phenylthiohydantoin-amino acids was accomplished by on-line HPLC using Buffer A containing 3.5% tetrahydrofuran in water with 18 ml of the Premix concentrate (Perkin Elmer/Applied Biosystems Division, Foster City, Calif.) containing acetic acid, sodium acetate, and sodium hexanesulfonate and Buffer B containing acetonitrile. Data was collected and analyzed on a Macintosh IIsi using Applied Biosystems 610 Data Analysis software.

Sequence determinations were made by visualizing chromatograms against a light source.

The major doublet band of the purified phospholipase B was N-terminally sequenced and found to contain the expected N-terminus SPVTSEYTSVREAPE (SEQ ID NO. 2). The doublet band from the whole broth culture was also subjected to N-terminal sequencing and was found to contain the predicted N-terminus (Ser-Pro-Val-Thr-Ser-Glu-Tyr-Thr-Ser-Val-Arg- . . . .), N-terminus-3 a.a's (Thr-Ser-Glu-Tyr-Thr- . . . .), and N-terminus-15 a.a's (Gly-Tyr-Lys-Pro-Gly-Ser- . . . .) (SEQ ID NO: 2).

Example 8

Thermostability Determination of Phospholipase B

A VP-DSC (MicroCal Inc., Amherst, Mass.) was employed according to the manufacturer's instructions to determine the thermostability of the phospholipase B under various pH conditions. Sample and reference solutions were carefully degassed immediately prior to loading of samples into the calorimeter. The reference contained buffer with no protein addition. Sample and reference solutions (approx. 0.5 ml) were thermally pre-equilibrated for 20 minutes at 5° C. prior to DSC scanning from 5° C. to 95° C. at a rate of 60° C. per hour.

Buffers consisted of 50 mM sodium acetate pH 4.5, 50 mM Tris-acetate pH 7, or 50 mM borate, pH 9. At pH 4.5 the protein displayed a single Td at 64.8° C.; at pH 7 the protein presented two transitions at 44.1° C. and 55.5° C., respectively; and at pH 9 the protein transition occurred at 35.5° C. Thus, the protein displayed the highest stability at pH 4.5.

Example 9

Characterization of Phospholipase B Activity

The assay for determination of lecithase and lysolecithase activity employed a NEFA C chromogenic assay (Wako Chemicals GmbH) for liberation of free fatty acids. Lecithin (Avanti Polar Lipids, 95% pure from plants) or lysolecithin (Sigma L4129, egg yolk) substrates were prepared at 10 mg per ml of distilled water and then diluted to 1 mg per ml in 20 mM HEPES pH 7 buffer. Lecithin dissolution required heating to 55° C. to prepare a suspension. The assay consisted of adding 10 μl of enzyme solution to 150 μl of the substrate solution. The reaction was incubated for ten minutes at 37° C. Following the incubation period analysis of liberated free fatty acids was performed. The lecithin substrate yielded no detectable colored product, but the lysolecithin substrate incubation resulted in a slight color.

A second assay was performed at pH 5 in 50 mM sodium acetate by incubating 10 μl of enzyme solution with 150 μl of 1 mg of lyolecithin per ml for one hour at 37° C. The reaction was stopped by the addition of 1 ml CHCl$_3$/ethyl acetate 1:9 v/v. The mixture was centrifuged and the supernatant was analyzed by reverse phase chromatography according to the method of Marcato and Cocchin, 1996, *J. Chromatogr.* A730: 83–90, with detection by light scattering. Incubation with lysolecithin resulted in the detection of a product peak with a retention time which corresponded to a palmitic acid standard.

DEPOSIT OF BIOLOGICAL MATERIAL

The following biological material has been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
| --- | --- | --- |
| *E. coli* pPH6 | NRRL B-30142 | Jun. 10, 1999 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. An isolated nucleic acid sequence encoding a polypeptide having phospholipase B activity comprising amino acids 20 to 464 of SEQ ID NO: 2.

2. The nucleic acid sequence of claim 1, which encodes a polypeptide comprising the amino acid sequence of SEQ ID NO: 2.

3. The nucleic acid sequence of claim 1, which encodes a polypeptide consisting of the amino acid sequence of SEQ ID NO: 2, or a fragment thereof which has phospholipase B activity.

4. The nucleic acid sequence of claim 3, which encodes a polypeptide consisting of amino acids 20 to 464 of SEQ ID NO: 2.

5. The nucleic acid sequence of claim 1, comprising the nucleic acid sequence of nucleotides 568 to 2045 of SEQ ID NO: 1.

6. The nucleic acid sequence of claim 1, contained in *E. coli* pPH6 as deposited with NRRL under accession number B-30142.

7. A nucleic acid construct comprising the nucleic acid sequence of claim 1 operably linked to one or more control sequences which direct the production of the polypeptide in a suitable expression host.

8. A recombinant expression vector comprising the nucleic acid construct of claim 7.

9. A recombinant host cell comprising the nucleic acid construct of claim 7.

10. A method for producing a polypeptide having phospholipase B activity comprising (a) cultivating a strain comprising the nucleic acid sequence of claim 1 under conditions suitable for producing the polypeptide; and (b) recovering the polypeptide.

11. A method for producing a polypeptide having phospholipase B activity comprising (a) cultivating the recombinant host cell of claim 9 under conditions suitable for production of the polypeptide; and (b) recovering the polypeptide.

12. A nucleic acid construct comprising a gene encoding a protein operably linked to a nucleic acid sequence encoding a signal peptide consisting of nucleotides 510 to 567 of SEQ ID NO: 1, wherein the gene is foreign to the nucleic acid sequence.

13. A recombinant expression vector comprising the nucleic acid construct of claim 12.

14. A recombinant host cell comprising the nucleic acid construct of claim 12.

15. A method for producing a protein comprising (a) cultivating the recombinant host cell of claim 14 under conditions suitable for production of the protein; and (b) recovering the protein.

* * * * *

SEQUENCE LISTING

<160> NUMBER OF SEQ ID NOS: 4

<210> SEQ ID NO 1
<211> LENGTH: 2318
<212> TYPE: DNA
<213> ORGANISM: Aspergillus oryzae

<400> SEQUENCE: 1
aattcctgga caacaatccc tttgagagtg atagtaaggg ggatgaactg agatgctaag    60

-continued

```
ctcacgttct tcgccttggc gtaggctgcc ccatgtcttg gtttagtgct tctctccacc    120
ctagtagctt agccattgct tgtccaatcc cattcccatc tcgcatcacg ctctatttat    180
gaccaaggct gtcaaatgag agccccactc atgtggcctc cacttcatat tgtttctttt    240
gtcgataaga ctgtcatccc gtctccggtg gcttccacga agaacgatttt gtaaagatgg   300
atagcgatag gctgcccttg gtcggtatga agccgaagtc cctcgtgcct cgatggatat    360
gcgcttcaac ccgacgcaca cgcacgtgg tatccgaatg ggacggaaag gtagctcctc     420
cagtgggcta tataagcctt tccctggccg ggctcagact ccctagcaag cagcattgtt    480
caagctcacg acctcaatcc gcgagtaaac atgaagtcca ccgctctgct tactggtctc    540
ggcctcttgg cctctctcgg tcttgctagc cctgtcacgt ccgagtatac gagcgtgcga    600
gaagccccctt tcgatacaa gcctggctcc aaggagtcca ttgagaactt gaaggacaag    660
gtcgagaaca ttgtctggct tattctcgag aacaggtttg tgtgcccctta cgatattcat   720
atgtggaata taaattcct caattcagct tgtggtatgt gaagacgagc actaacatat     780
ggtccagatc cttcgataac attctgggag gcgtgcgccg ccaaggactg gacaaccccga   840
tcaacaacgg cccgttctgc aactacaaga atgcgagcga cccatcctcg ggcaagtact    900
gtactcaggc caaggactat gattccgtgt tcaacgatcc agaccactcc gtgactggta    960
ataacttgga gttctacgga acttacaccc caaacaatgg tgcgattgcc agtggcaagg   1020
tcgtcgccga ccagtctggc ttcctcaacg cacagcttaa cgactacccc aaactggccc   1080
cagaagaggc gacaaggcaa gtgatgggat actatacgga ggaggaggtt cctacgctcg   1140
tggaccttgt ggatgagttc actactttca acagctggtt ctcgtgtgtt cctggcgtaa   1200
gtgcgataaa tctgtatatt tttaattttg actaacgcgt tcaaaagcct accaacccca   1260
accgcttgtg cgctctggca ggaaccgctg ctgggcatgg caagaatgac gatgacttcc   1320
tgaactatgg tatctctagc aagtccatct tcgaggccgc caacgagaag ggcgtgtcct   1380
ggctcaacta cgatggcacc aacggagaat tcgaaccgga ttctctcttc ttcacctacg   1440
tcaaccagac ctcccggtcc aacgtggtgc ccgttgaaaa cttcttccaa gacgcctacc   1500
tcggtgtcct ccctaaattc tcttacatta acccctcctg ctgcggcacc aacaccaact   1560
ccatgcaccc caccggtaac gtctcctacg gtgaggtctt cgtcaagcag atctatgatg   1620
ccattcgcca gggccctcag tgggacaaga ccctgctctt cattacctac gacgagaccg   1680
gtggcttcta cgaccatgtc cctcccccctc tcgccgtccg cccggacaac ctgacctaca   1740
ctgagactgc gaagaacggt cagaaataca ctcttcactt cgaccgtctg ggtggccgca   1800
tgccgacctg ggttatctcc ccttacagta agaagggata catcgagcag tacgaacgg    1860
atcccgtcac gggcaagccc gctccctaca gtgctacctc cgtcctcaag actctcggat   1920
atctctggga catcgaggac ttcacccctc gtgtcgccca ctctccatct ttcgatcacc   1980
tgatcggcac gactttgcgt gaggatgctc ctattgctct caagactccc catacctttt   2040
cggtataagt ctcagtccgt gcagtgagac aggattaaaa gtgatgatga acgttctgac   2100
ttcagtgaac gattacatgt tatagagcat tgttttgctt atagctacgc ctagagcgag   2160
cgcgatgatg ataagataaa gctgggttat ttctctattg tatattcatt aatgaaagac   2220
tttgataaca tgggattaa aaggaaatg ttttcttgca caatcaactc acggaacagg     2280
cgtaactta cgatgactgc accccggata cattaatt                            2318
```

<210> SEQ ID NO 2
<211> LENGTH: 464

```
<212> TYPE: PRT
<213> ORGANISM: Aspergillus oryzae

<400> SEQUENCE: 2

Met Lys Ser Thr Ala Leu Leu Thr Gly Leu Gly Leu Leu Ala Ser Leu
 1               5                  10                  15

Gly Leu Ala Ser Pro Val Thr Ser Glu Tyr Thr Ser Val Arg Glu Ala
                20                  25                  30

Pro Phe Gly Tyr Lys Pro Gly Ser Lys Glu Ser Ile Glu Asn Leu Lys
            35                  40                  45

Asp Lys Val Glu Asn Ile Val Trp Leu Ile Leu Glu Asn Arg Ser Phe
        50                  55                  60

Asp Asn Ile Leu Gly Gly Val Arg Arg Gln Gly Leu Asp Asn Pro Ile
65                  70                  75                  80

Asn Asn Gly Pro Phe Cys Asn Tyr Lys Asn Ala Ser Asp Pro Ser Ser
                85                  90                  95

Gly Lys Tyr Cys Thr Gln Ala Lys Asp Tyr Asp Ser Val Phe Asn Asp
            100                 105                 110

Pro Asp His Ser Val Thr Gly Asn Asn Leu Glu Phe Tyr Gly Thr Tyr
        115                 120                 125

Thr Pro Asn Asn Gly Ala Ile Ala Ser Gly Lys Val Val Ala Asp Gln
    130                 135                 140

Ser Gly Phe Leu Asn Ala Gln Leu Asn Asp Tyr Pro Lys Leu Ala Pro
145                 150                 155                 160

Glu Glu Ala Thr Arg Gln Val Met Gly Tyr Tyr Thr Glu Glu Val
                165                 170                 175

Pro Thr Leu Val Asp Leu Val Asp Glu Phe Thr Thr Phe Asn Ser Trp
            180                 185                 190

Phe Ser Cys Val Pro Gly Pro Thr Asn Pro Asn Arg Leu Cys Ala Leu
        195                 200                 205

Ala Gly Thr Ala Ala Gly His Gly Lys Asn Asp Asp Asp Phe Leu Asn
    210                 215                 220

Tyr Gly Ile Ser Ser Lys Ser Ile Phe Glu Ala Ala Asn Glu Lys Gly
225                 230                 235                 240

Val Ser Trp Leu Asn Tyr Asp Gly Thr Asn Gly Glu Phe Glu Pro Asp
                245                 250                 255

Ser Leu Phe Phe Thr Tyr Val Asn Gln Thr Ser Arg Ser Asn Val Val
            260                 265                 270

Pro Val Glu Asn Phe Phe Gln Asp Ala Tyr Leu Gly Val Leu Pro Lys
        275                 280                 285

Phe Ser Tyr Ile Asn Pro Ser Cys Cys Gly Thr Asn Thr Asn Ser Met
    290                 295                 300

His Pro Thr Gly Asn Val Ser Tyr Gly Glu Val Phe Val Lys Gln Ile
305                 310                 315                 320

Tyr Asp Ala Ile Arg Gln Gly Pro Gln Trp Asp Lys Thr Leu Leu Phe
                325                 330                 335

Ile Thr Tyr Asp Glu Thr Gly Gly Phe Tyr Asp His Val Pro Pro Pro
            340                 345                 350

Leu Ala Val Arg Pro Asp Asn Leu Thr Tyr Thr Glu Thr Ala Lys Asn
        355                 360                 365

Gly Gln Lys Tyr Thr Leu His Phe Asp Arg Leu Gly Gly Arg Met Pro
    370                 375                 380

Thr Trp Val Ile Ser Pro Tyr Ser Lys Lys Gly Tyr Ile Glu Gln Tyr
385                 390                 395                 400
```

```
Gly Thr Asp Pro Val Thr Gly Lys Pro Ala Pro Tyr Ser Ala Thr Ser
            405                 410                 415

Val Leu Lys Thr Leu Gly Tyr Leu Trp Asp Ile Glu Asp Phe Thr Pro
            420                 425                 430

Arg Val Ala His Ser Pro Ser Phe Asp His Leu Ile Gly Thr Thr Leu
            435                 440                 445

Arg Glu Asp Ala Pro Ile Ala Leu Lys Thr Pro His Thr Phe Ser Val
            450                 455                 460

<210> SEQ ID NO 3
<211> LENGTH: 27
<212> TYPE: DNA
<213> ORGANISM: Aspergillus oryzae

<400> SEQUENCE: 3
atttaaatga tgaagtccac cgctctg                                    27

<210> SEQ ID NO 4
<211> LENGTH: 30
<212> TYPE: DNA
<213> ORGANISM: Aspergillus oryzae

<400> SEQUENCE: 4
gttaattaaa cttataccga aaaggtatgg                                 30
```